US008794049B1

(12) United States Patent
Norkin et al.

(10) Patent No.: US 8,794,049 B1
(45) Date of Patent: Aug. 5, 2014

(54) REAL-TIME MONITOR FOR WINE FERMENTATION

(76) Inventors: Marci Norkin, Pasadena, CA (US); Steven D. Colome, Newport Beach, CA (US)

( * ) Notice: Subject to any disclaimer, the term of this patent is extended or adjusted under 35 U.S.C. 154(b) by 95 days.

(21) Appl. No.: 13/358,499

(22) Filed: Jan. 25, 2012

Related U.S. Application Data

(60) Provisional application No. 61/436,230, filed on Jan. 26, 2011.

(51) Int. Cl.
*G01M 3/02* (2006.01)
*C12M 1/34* (2006.01)

(52) U.S. Cl.
USPC .......................................... 73/37; 435/287.1

(58) Field of Classification Search
CPC .................................. G01F 23/14; G01M 3/26
USPC .................. 435/32, 287.1, 286.5, 288.7, 813; 73/29.01, 29.03, 31.04, 37
See application file for complete search history.

(56) References Cited

U.S. PATENT DOCUMENTS

| | | | | |
|---|---|---|---|---|
| 4,359,533 A | * | 11/1982 | Wilke et al. | 435/161 |
| 4,856,421 A | * | 8/1989 | Whitford | 99/276 |
| 4,883,759 A | * | 11/1989 | Hopkins | 435/295.1 |
| 4,959,228 A | * | 9/1990 | Skrgatic et al. | 426/11 |
| 5,245,405 A | * | 9/1993 | Mitchell et al. | 356/301 |
| 5,470,746 A | * | 11/1995 | Kim | 435/287.1 |
| 6,010,909 A | * | 1/2000 | Lapidus | 436/63 |
| 7,510,864 B2 | * | 3/2009 | Krichevsky et al. | 435/286.5 |
| 2004/0004717 A1 | * | 1/2004 | Reed | 356/338 |
| 2004/0039514 A1 | * | 2/2004 | Steichen et al. | 701/109 |
| 2004/0076712 A1 | * | 4/2004 | Rodgers et al. | 426/11 |
| 2007/0238169 A1 | * | 10/2007 | Abilez et al. | 435/325 |
| 2007/0266632 A1 | * | 11/2007 | Tsangaris et al. | 48/190 |
| 2008/0193207 A1 | * | 8/2008 | Kruse et al. | 403/133 |
| 2008/0213874 A1 | * | 9/2008 | Mitchell et al. | 435/287.1 |
| 2009/0223612 A1 | * | 9/2009 | McKnight et al. | 149/21 |
| 2013/0140231 A1 | * | 6/2013 | Novak et al. | 210/603 |

* cited by examiner

*Primary Examiner* — Hezron E Williams
*Assistant Examiner* — David Z Huang
(74) *Attorney, Agent, or Firm* — Wallace G. Walter

(57) ABSTRACT

A system is provided for real-time, continuous, and accurate monitoring of the various states of the fermentation process in a closed fermentation vessel by monitoring the pressure created by the flow of carbon dioxide that is evolved as a consequence of the fermentation activity. The carbon dioxide transits through an orifice that has a flow area sufficient to maintain pressure in a range suitable for a pressure sensor with the electrical output thereof transmitted to an instrument that records and displays the pressure data to provide state information for use in algorithms to establish pre-alert warnings or alarms and provide correction control signals to ameliorate any anomalous condition detected.

4 Claims, 4 Drawing Sheets

REAL-TIME MONITOR FOR WINE FERMENTATION

CROSS-REFERENCE TO RELATED APPLICATION

This application claims the benefit of U.S. Provisional patent application 61/436,230 filed Jan. 26, 2011 by the applicants herein, the disclosure of which is incorporated herein by reference.

The present invention relates to the monitoring of the successive states or stages of the fermentation and, more particularly, to fermentation monitoring during active yeast-based fermentation in the production of alcohol-containing wine and other fermented subject matter, including pharmaceuticals, and, still more particularly, to monitoring of closed fermentation vessels in which carbon dioxide is released though a port or release valve as sugar is consumed and ethanol produced.

During the production of wine, a mixture of crushed grapes, juice, and yeast is placed in a fermentation vessel; the yeast metabolizes sugars in the grape juice (known as "must") over a period of several days to one or two weeks at a process temperature of about 60-90° F. During this fermentation period in which the liquid component of the must evolves into the new wine, both EtOH and $CO_2$ evolve in equal molar amounts as a consequence of yeast metabolism. Governed by the chemical properties of solubility, vapor pressures in the headspace, and other chemical and physical properties, the ethanol and the carbon dioxide enter the headspace within the fermentation vessel above the surface of the must.

$CO_2$ and EtOH co-evolve during the fermentation process with the volume thereof varying with time; thus, the fermentation process can be described as having many successive "states" or "stages". During the very beginning of the fermentation process after initial yeast-innoculation, the generation of $CO_2$ and EtOH is low with the volumes thereof increasing to some maximum as the process temperature rises and the sugars are consumed at some time-varying rate with the volume of $CO_2$ and EtOH thereafter diminishing as the fermentation process is completed. Historically, fermentation activity at any stage in the process has been measured by assaying samples for Brix reduction and/or by measuring temperature as a function of time. Neither Brix assaying or temperature measurement can be viewed as "real time" since the Brix assay is a chemical analysis process that is completed sometime after the sample is taken and the substantial heat capacity of the liquid components introduces a "thermal hysteresis" variable into the process. Additionally, Brix assaying and/or temperature measurements suffer from inhomogeneity within the fermentation tank and are subject to sampling error. Thus, Brix assaying and/or temperature measurement are sub-optimal metrics for identifying a particular state or stage of the fermentation process. In general, Brix assaying and/or temperature measurements cannot accurately identify sluggish fermentations, over-active fermentations, or sub-optimal equipment functionality (or equipment failures) quickly enough to allow for effective corrective action(s) by the wine maker to save or preserve the quality of the new wine.

SUMMARY

Successive pressure measurements are taken from the start of the fermentation process by a stored-program controlled microprocessor fermentation tracking instrument with the successive data points compared to reference or known good data points with the variance indicative of a normal fermentation process, a slow or sluggish fermentation process, or an over-active fermentation process. In those instances in which a non-normal fermentation is identified, corrective action can be initiated to correct the non-normal condition. In those cases, where successive pressure measurements multiple concurrent processes, comparison of data points between the different concurrent processes can identify an anomalous process and provide an alert signal or a corrective control signal for that anomalous process.

The benefit of using carbon dioxide to monitor fermentation activity is that the carbon dioxide is released immediately after it is produced during the sugar metabolism process and the flow thereof through the exhaust port or release valve of a closed fermentation vessel integrates activity throughout the must volume.

DESCRIPTION OF THE PREFERRED EMBODIMENT

Figure 1:
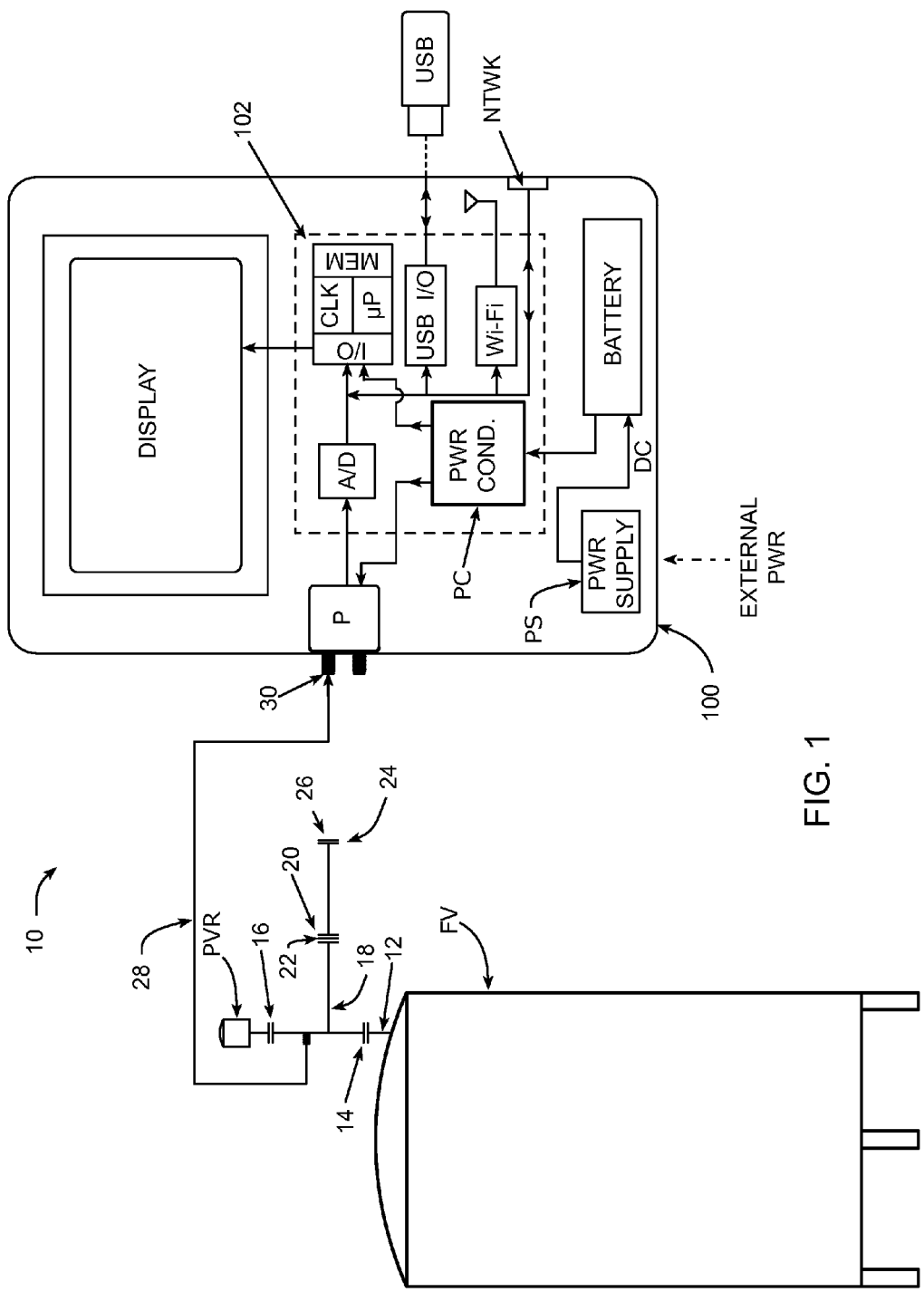
FIG. 1 is an overall system schematic of a fermentation vessel and a pressure sensing and process control instrument.

FIG. 1 illustrates an exemplary system and is designated generally therein by the reference character 10. A fermentation vessel FV includes various viewing/inspection ports, hatches, and closable openings (not shown) and is typically fabricated from stainless steel, copper, or other suitable materials with a working volume or capacity of up to 600,000 gallons or more. In practice, the lower portion of the interior volume of the fermentation vessel FV is filled to some level with liquid grape or other fruit extracts, hops, grains, and/or other fermentable feedstocks along with any other materials/additives typically used in the process. A headspace is left above the surface of the liquid into which water vapor, ethanol, $CO_2$, and other gases or vapors associated with the fermentation process accumulate as they are evolved during the fermentation process; in general, an equilibria is established between the liquid component and the gaseous/vaporous components in the headspace. In the fermentation process for wine, the yeast component metabolizes sugars in the starting material with the process proceeding on a day-by-day basis until completion. The fermentation process generates $CO_2$ and EtOH in direct proportion to one another in the liquid must with the gases/vapors in the headspace at a temperature of 60-90° F. or so during the process.

As shown in FIG. 1, a bleed-off conduit 12 is connected to the top of the fermentation vessel FV and is in fluid communication with the headspace within the fermentation vessel FV so that the pressure of the gases/vapors in the headspace can be measured as described below. The bleed-off conduit 12 includes a first connection interface 14 (typically mating flanges that are connected together by threaded fasteners) and another connection interface 16 that connects to a pressure-vacuum relief valve PVR that functions as a primary safety device for the fermentation vessel FV. A vent line 18 branches from the bleed-off conduit 12 to a connection interface 20 that includes a orifice plate 22 positioned between the flanges thereof and to a vent 24 that includes a vent screen 26. Gases/vapors in the headspace that pass through the orifice plate 22 are vented to the atmosphere through the vent screen 26 at a orifice-constrained flow rate. In addition, a pressure sense line 28 provides fluid communication with a input port 30 of a pressure sensing and process control instrument 100 as described below.

Figure 2:
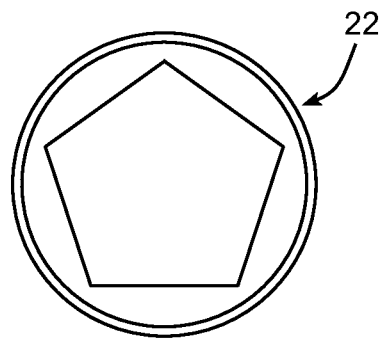
FIG. 2 is an elevational view of a first orifice plate.
Figure 3:
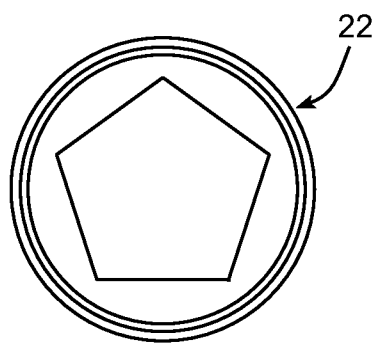
FIG. 3 is an elevational view of a second orifice plate.
Figure 4:
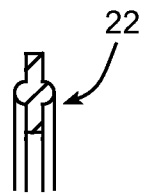
FIG. 4 is a side view, in cross-section, of a portion of the rim of an orifice plate.
Figure 5:
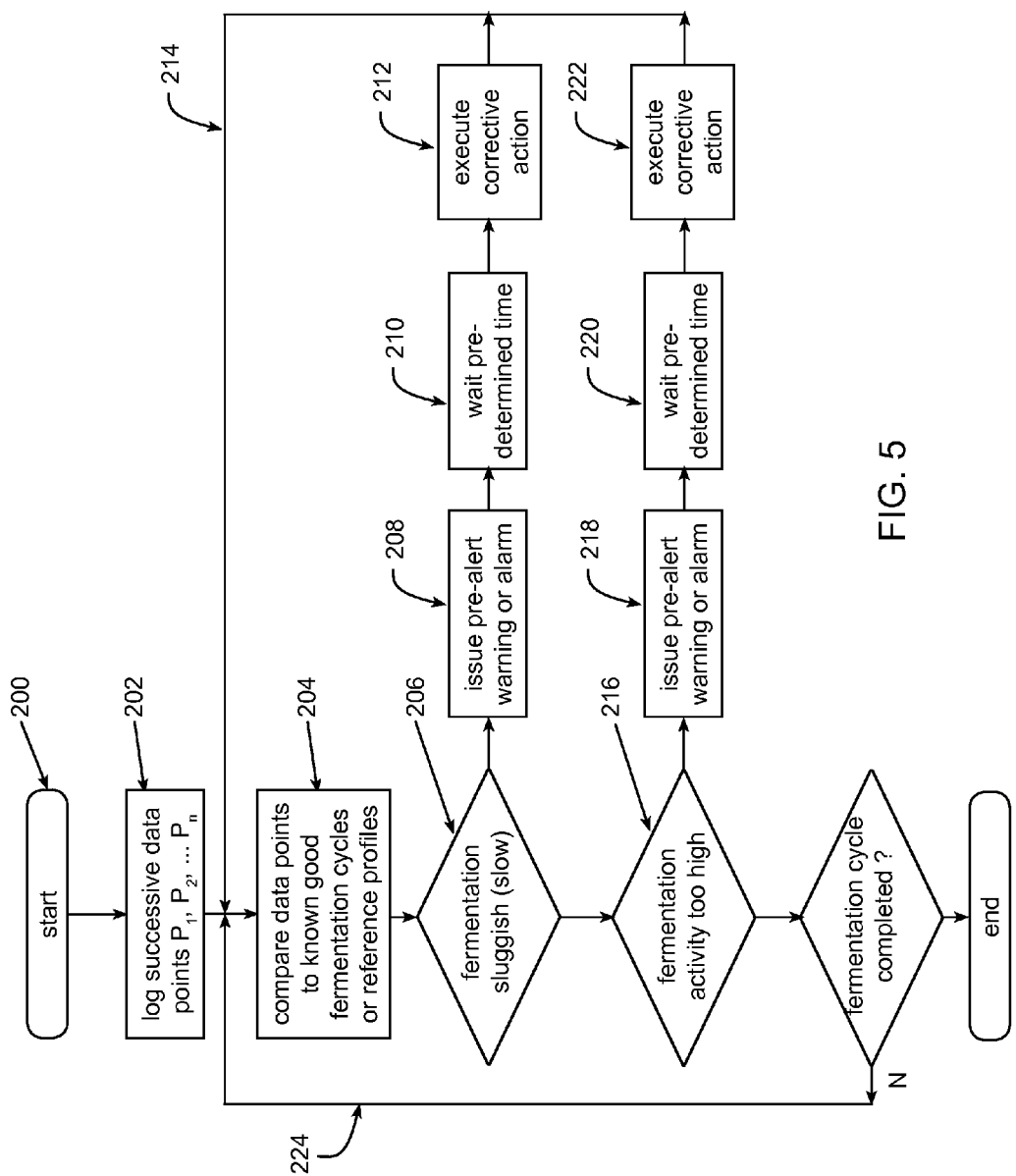
FIG. 5 is an example process flow diagram illustrating operation of the pressure sensing and process control instrument.

As shown in FIGS. 2 and 3, the orifice plate 22 has a generally circular outline that conforms dimensionally to the flanges of the connection interface 20 and is provided with a pentagonal orifice. As shown in FIG. 5, the rim of the orifice plate 22 is thinned on both sides for optimum mating with the connection interface 20. In general, the orifice plate 22 is fabricated from a PTFE ("Teflon") material or equivalent with the orifice functioning to constrain the flow of any gases/vapors from the headspace so as to maintain a pressure range that is appropriately matched to a pressure sensor in the pressure sensing and process control instrument 100, as explained in more detail below. As shown in the following table and for the standard connection interface sizes (i.e., 2-, 3-, and 4-inch fittings) the orifice plate 22 can include a 60% opening and a 75% opening; in the table below, the length of one of the five linear sides of the pentagonal orifice is presented for the three common fitting diameters and for the 60% and the 75% opening choices.

| Connector Interface | 60% open | 75% open |
| --- | --- | --- |
| 2-inch | 0.981" | 1.097" |
| 3-inch | 1.505" | 1.682" |
| 4-inch | 2.028" | 2.267" |

While the preferred embodiment of the orifice plate 22 uses a pentagonal orifice to prevent or minimize audible "whistling," other orifice shapes are suitable, including a circular orifice.

A preferred embodiment of a pressure sensing and process control instrument 100 includes a pressure sensor P designed to sense pressures in the range of those typically experienced during the fermentation process; a suitable pressure sensor P is available from Setra Systems, Inc. of Boxborough Mass. 01719 under the Model 2651025WD2BT1C differential pressure transducer and having a 0-25" $H_2O$ operating range. The output of the pressure sensor P is provided as an analog value to a processing circuit 102 that includes an analog/digital converter ND, a microprocessor μP, a display D, a power conditioner PC, a USB interface, a wireless communication link, such as a 802.11a, b, and/or g Wi-Fi link (as well a successor standards), and a network interface (i.e., RJ-45 connector). Additionally, the pressure sensing and process control instrument 100 includes a power supply PS that supplies DC power to a rechargeable battery (i.e., Li-ion), which, in turn, provides power to a power conditioner PC that conditions the battery power for the pressure sensor P and the microprocessor μP as well as the analog/digital converter ND, the USB port, the Wi-Fi link, and the network interface. The microprocessor μP includes parallel and/or serial digital inputs, an on-chip central processing unit, a clock CLK, various registers, and on-chip memory for storing firmware and/or software and data. Suitable processors include general purpose programmable processors having various bit-width buses (8-bit, 16-bit, etc.) as well special purpose processors including RISC processors and programmable logic arrays. While not shown, additional memory may be provided within the processing circuit 102 for the storage of data including long-term data history.

The microprocessor μP executes its firmware or software cycle as shown in a generalized fashion in FIG. 5; as shown, the sequence is started at 200 followed by the logging of successive data points at pre-selected time intervals. The sensing and logging data $P_1, P_2, \ldots P_n$ can take place, for example, every 10 minutes. In addition to storing each successive data point, the successive data points can be displayed as a graph over time on the display D. When a sufficient number of data points are logged, the data points can be compared to data points from a reference or exemplar fermentation cycle or from one or more known good data points from prior fermentation cycles. As can be appreciated, reference fermentation cycles or data from known good prior fermentation cycles for various types of starting materials, fermentation vessel capacities, etc. can be stored in a library kept in memory. As shown at step 206, if the data point comparisons show a trend toward slow (i.e., "sluggish") fermentation, a pre-alert warning or an alarm can be issued (based upon the variance between the measured data points and the exemplars) and, if the wine maker does not intervene to correct the situation after a suitable waiting period (step 210), some type of corrective action and be taken at step 212. In the case of a slow fermentation that results from an inhomogeniety of the contents of the fermentation vessel, mixers can be operated to mix the contents of the fermentation vessel or pumps activated to pump material from the bottom of the fermentation vessel to the upper portions thereof with the processing sequence returning via pathway 214 to step 204 to repeat the measuring and comparing cycle. Conversely, if the data point comparisons show a trend toward a high activity fermentation, a pre-alert warning or an alarm can be issued at step 218 (based upon the variance between the measured data points and the exemplars) and, if the wine maker does not intervene to correct the situation after a suitable waiting period (step 220), some type of corrective action can be taken can be taken at step 222. In the case of a high activity fermentation, cooling jackets surrounding the fermentation vessel can be activated to lower the temperature of the mix and thereby lower the fermentation activity with the processing sequence returning via pathway 214 to step 204 to repeat the measuring and comparing cycle. In the event the fermentation process is within expected bounds, the process simply loops via pathway 224 until the fermentation cycle is completed.

Figure 6:
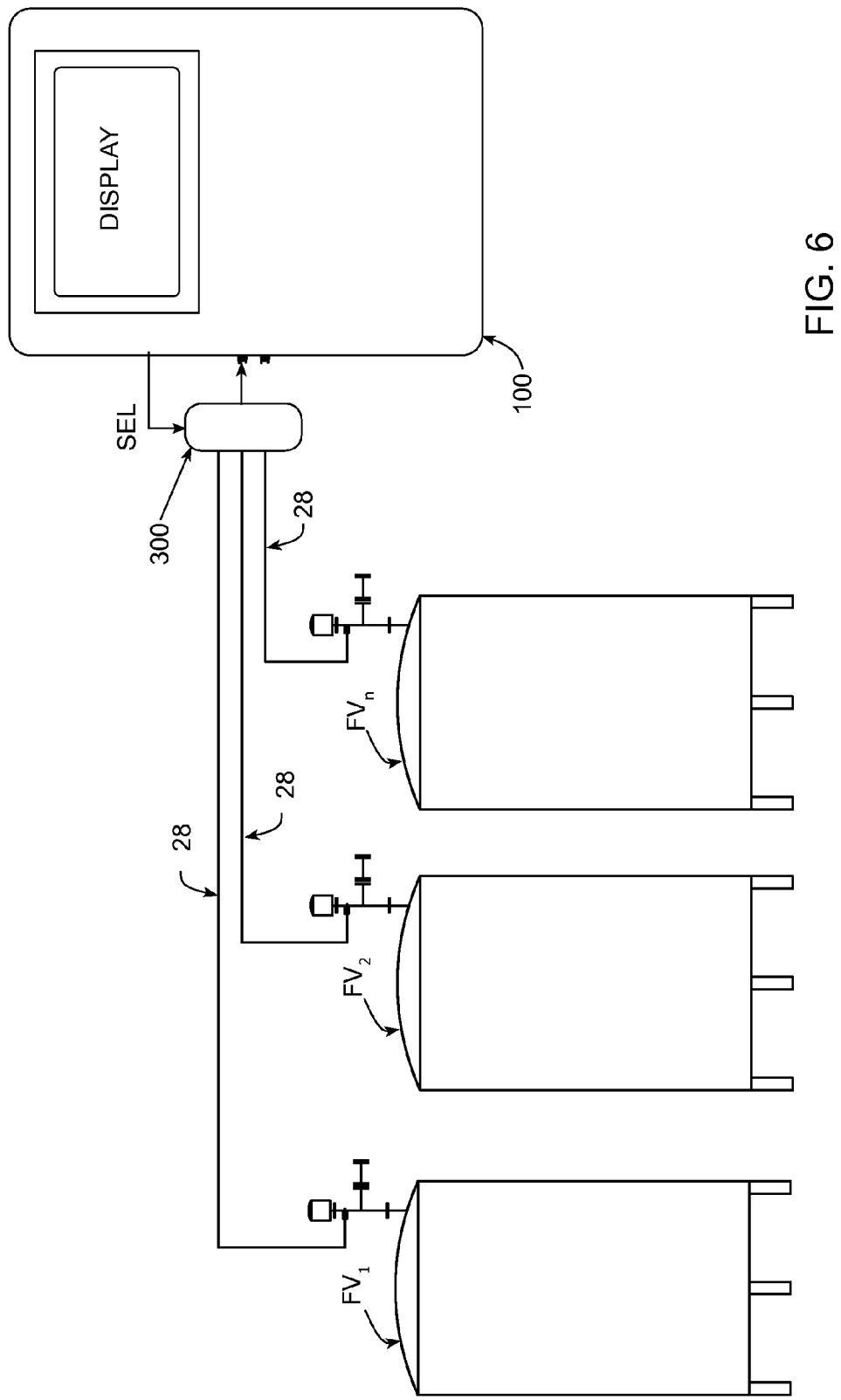
FIG. 6 is an overall system schematic of a multi-fermentation vessel system.

While the preferred embodiment has been shown as a single fermentation vessel FV, as can appreciated, multi-fermentation vessel systems are possible and as shown in FIG. 6, the pressure sense line 28 from n fermentation vessels $FV_1, FV_2, \ldots FV_n$ connect to a 1-of-n manifold 300 by which a selection signal from the pressure sensing and process control instrument 100 sequentially selects each fermentation vessel $FV_1, FV_2, \ldots FV_n$ for data logging.

Since the pressure sensing and process control instrument 100 includes a USB port, all data collected by the pressure sensing and process control instrument 100 can be downloaded for storage or transfer to another device. Additionally, data can be transmitted over the Wi-Fi link to a hub for uploading to a central computer or transferred by the network ethernet port (RJ-45) that can include Internet functionality. As can be appreciated, the Wi-Fi link and the network link also facilitate transmission of pre-alert warnings or alarms to a pager, cellphone, or smartphone as needed.

As will be apparent to those skilled in the art, various changes and modifications may be made to the illustrated embodiment of the present invention without departing from the spirit and scope of the invention as determined in the appended claims and their legal equivalent.

The invention claimed is:

1. A system for measuring the state or states of a fermentation cycle in a fermentation vessel for producing an alcohol-containing beverage, the fermentation vessel having a liquid therein undergoing fermentation in which at least a carbon dioxide gas is evolved into a headspace of the fermentation vessel at a rate that is proportionate to the state of the fermentation cycle, comprising:
   a pressure transducer measuring pressure in the headspace and providing an electrical signal therefrom representing the so-measured pressure;
   a stored-program microprocessor for receiving the electrical signal from the pressure transducer and logging the so-sensed pressure data and comparing the so-sensed pressure data with reference data to identify an anomalous condition including at least one of a group of anomalous conditions comprising at least a slow fermentation condition and a high-activity fermentation condition and issuing a signal to effect a corrective action increasing fermentation activity upon identification of a slow fermentation condition or to effect a corrective action decreasing fermentation activity upon identification of high-activity fermentation.

2. The system of claim 1 wherein a pre-alert warning or alarm is issued upon identification of a one of said slow fermentation condition or a high-activity fermentation.

3. The system of claim 1 wherein a slow fermentation corrective action comprises mixing the liquid in the fermentation vessel.

4. The system of claim 1 wherein a high-activity fermentation corrective action comprises cooling the liquid in the fermentation vessel.

* * * * *